United States Patent
Friedrichs et al.

(10) Patent No.: US 10,582,962 B2
(45) Date of Patent: Mar. 10, 2020

(54) SYSTEM AND METHOD FOR HARMONIC CONTROL OF DUAL-OUTPUT GENERATORS

(71) Applicants: COVIDIEN LP, Mansfield, MA (US); UNIVERSITY OF TENNESSEE RESEARCH FOUNDATION, Knoxville, TN (US)

(72) Inventors: Daniel A. Friedrichs, Aurora, CO (US); Chongwen Zhao, Knoxville, TN (US); Bradford C. Trento, Knoxville, TN (US); Daniel J. Costinett, Knoxville, TN (US)

(73) Assignee: Covidien LP, Mansfield, MA (US)

(*) Notice: Subject to any disclaimer, the term of this patent is extended or adjusted under 35 U.S.C. 154(b) by 672 days.

(21) Appl. No.: 15/004,923

(22) Filed: Jan. 23, 2016

(65) Prior Publication Data

US 2017/0209202 A1 Jul. 27, 2017

(51) Int. Cl.
*A61B 18/14* (2006.01)
*A61B 18/12* (2006.01)
(Continued)

(52) U.S. Cl.
CPC .. *A61B 18/1206* (2013.01); *A61B 17/320092* (2013.01); *A61B 18/14* (2013.01); *A61B 18/1445* (2013.01); *H02M 7/5395* (2013.01); *A61B 18/16* (2013.01); *A61B 2017/320094* (2017.08); *A61B 2017/320095* (2017.08); *A61B 2018/0063* (2013.01);
(Continued)

(58) Field of Classification Search
CPC ...... A61B 2018/128; A61B 2018/1266; A61B 18/1206; A61B 2018/00994; A61B 17/320092; A61B 18/1445; A61B 18/14; A61B 2018/0063; A61B 2018/00601; A61B 2018/00589; A61B 2018/00577; A61B 18/16; H02M 7/5395
See application file for complete search history.

(56) References Cited

U.S. PATENT DOCUMENTS

| 5,630,822 A | 5/1997 | Hermann et al. |
| 5,735,289 A | 4/1998 | Pfeffer et al. |

(Continued)

FOREIGN PATENT DOCUMENTS

| CN | 102665585 A | 9/2012 |
| CN | 103403473 A | 11/2013 |

(Continued)

OTHER PUBLICATIONS

Japanese Office Action dated Mar. 15, 2018 issued in corresponding Japanese Application No. 1 2017-007701.
(Continued)

*Primary Examiner* — Jaymi E Della
*Assistant Examiner* — Sean W Collins

(57) ABSTRACT

A dual-output generator is configured to output two or more waveforms at different frequencies. In particular, the dual-output generator is configured to provide low-frequency output, which may be suitable for ultrasonic surgical instruments, and a high-frequency output, which may be suitable for electrosurgical instruments, while reducing the amplitude of all remaining frequencies other than the two selected low and high frequencies to about zero.

19 Claims, 6 Drawing Sheets

(51) Int. Cl.
   *A61B 17/32* (2006.01)
   *H02M 7/5395* (2006.01)
   *A61B 18/00* (2006.01)
   *A61B 18/16* (2006.01)

(52) U.S. Cl.
   CPC .............. *A61B 2018/00577* (2013.01); *A61B 2018/00589* (2013.01); *A61B 2018/00601* (2013.01); *A61B 2018/00994* (2013.01); *A61B 2018/128* (2013.01); *A61B 2018/1266* (2013.01)

(56) References Cited

U.S. PATENT DOCUMENTS

| | | | |
|---|---|---|---|
| 5,954,686 | A | 9/1999 | Garito et al. |
| 6,134,127 | A * | 10/2000 | Kirchberg ............... H02M 1/12 363/41 |
| 6,270,505 | B1 | 8/2001 | Yoshida et al. |
| 8,652,125 | B2 | 2/2014 | Keller |
| 8,998,939 | B2 | 4/2015 | Price et al. |
| 9,192,423 | B2 | 11/2015 | Schall et al. |
| 2002/0068931 | A1* | 6/2002 | Wong ................ A61B 18/1206 606/34 |
| 2007/0225699 | A1 | 9/2007 | Goble et al. |
| 2010/0114090 | A1* | 5/2010 | Hosier .................. A61B 18/12 606/33 |
| 2012/0081061 | A1* | 4/2012 | Zargari ..................... H02J 3/01 318/503 |
| 2013/0305760 | A1* | 11/2013 | Shinomoto ........... F25B 49/025 62/238.7 |
| 2013/0325380 | A1 | 12/2013 | Behnke, II et al. |
| 2015/0223865 | A1 | 8/2015 | Krapohl et al. |
| 2015/0357938 | A1* | 12/2015 | Yamasaki ............... H02P 27/00 363/41 |
| 2016/0317178 | A1* | 11/2016 | Green ............ A61B 17/320068 |
| 2017/0189096 | A1* | 7/2017 | Danziger ............... A61B 90/98 |
| 2017/0302154 | A1* | 10/2017 | Tada ....................... H02M 1/08 |

FOREIGN PATENT DOCUMENTS

| | | |
|---|---|---|
| DE | 9218154 U1 | 9/1993 |
| EP | 2485670 A2 | 8/2012 |
| EP | 2674694 A1 | 12/2013 |
| EP | 2829248 A1 | 1/2015 |
| JP | 3-111036 B2 | 11/2000 |
| JP | 2002-306507 A | 10/2002 |
| JP | 2013512056 A | 4/2013 |
| JP | 2014500058 A | 1/2014 |
| WO | 0211627 A2 | 2/2002 |
| WO | 2003073949 A1 | 9/2003 |
| WO | 2015094749 A1 | 6/2015 |

OTHER PUBLICATIONS

European Search Report dated Aug. 17, 2017 issued in corresponding European Application No. 17152397.0 (date of completion Jun. 28, 2017).

European Search Report dated Aug. 17, 2017 issued in corresponding European Application No. 17152397.0 (date of completion Aug. 9, 2017).

Japanese Office Action dated Sep. 22, 2017 issued in corresponding JP Appln. No. 2017-007701.

Japanese Notice of Allowance dated Aug. 20, 2018 issued in corresponding JP Appln. No. 2017-007701. (Summary only).

Chinese Office Action dated Nov. 6, 2018 issued in corresponding Chinese Appln. No. 201710057101.6.

The extended European Search Report dated Nov. 27, 2018 issued in corresponding EP Appln. No. 18193703.8.

Chinese Office Action dated Jul. 2, 2019 issued in corresponding CN Appln. No. 201710057101.6.

* cited by examiner

SYSTEM AND METHOD FOR HARMONIC CONTROL OF DUAL-OUTPUT GENERATORS

BACKGROUND

Technical Field

The present disclosure relates to systems and methods for simultaneously powering surgical energy devices at multiple frequencies. In particular, the present disclosure relates to a generator configured to simultaneously power one or more outputs at specified frequencies and regulated amplitude suitable for powering a first device at a first frequency and a second device at a second frequency, which is different from the first frequency.

Background of Related Art

Electrosurgery involves application of high radio frequency ("RF") electrical current to a surgical site to cut, ablate, desiccate, or coagulate tissue. In monopolar electrosurgery, a source or active electrode delivers radio frequency alternating current from the RF generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like.

Ultrasonic surgical devices have also been demonstrated to provide hemostasis and efficient dissection of tissue with minimum lateral thermal damage and low smoke generation. Unlike electrosurgical devices, which require electrical current to flow through a patient, ultrasonic surgical devices operate by applying mechanical motion through an ultrasonic probe using an ultrasonic transducer that is driven at a resonant frequency.

Each of the electrosurgical and ultrasonic devices has their desired uses due to their inherent operational characteristics. Accordingly, there is a need for a system and a generator configured to operate both types of the instruments simultaneously to provide for new and improved surgical techniques and applications.

SUMMARY

The present disclosure provides a dual-output generator configured to output two or more waveforms at different frequencies allowing the dual-output generator to provide low-frequency output, which may be suitable for ultrasonic surgical instruments, and a high-frequency output, which may be suitable for electrosurgical instruments, while reducing the amplitude of all remaining frequencies other than the two selected low and high frequencies to about zero.

According to an embodiment of the present disclosure, a dual-output electrosurgical generator is provided. The generator includes a power supply configured to output a DC waveform and an inverter coupled to the power supply. The inverter includes at least one switching element operated at a switching angle. The generator also includes a controller coupled to the inverter and configured to modulate the switching angle to generate a first waveform at a first frequency and a secondary waveform at a second frequency.

According to another embodiment of the present disclosure, an electrosurgical system is provided. The system includes a dual-output electrosurgical generator having a power supply configured to output a DC waveform and an inverter coupled to the power supply. The inverter includes at least one switching element operated at a switching angle. The generator also includes a controller coupled to the inverter and configured to modulate the switching angle to generate a first waveform at a first frequency and a secondary waveform at a second frequency. The generator further includes a first output outputting the first waveform and a second output outputting the second waveform. The system also includes a first instrument coupled to the first output and energizable by the first waveform and a second instrument coupled to the second output and energizable by the second waveform.

According to an aspect of the above-described embodiment, the first instrument is an ultrasonic instrument including a transducer energizable by the first waveform and the second instrument is an electrosurgical instrument including at least one electrode configured to contact tissue and transmit the second waveform thereto.

According to one aspect of the above-described embodiment, the first instrument is a first electrosurgical instrument including at least one first electrode configured to contact tissue and transmit the first waveform thereto and the second instrument is a second electrosurgical instrument including at least second one electrode configured to contact tissue and transmit the second waveform thereto.

According to an aspect of any of the above-described embodiments, the first frequency is a fundamental frequency, the second frequency is a harmonic frequency of the fundamental frequency, and the second frequency is higher than the first frequency.

According to another aspect of any of the above-described embodiments, the generator further includes a low-frequency filter coupled to the inverter and configured to output the first waveform and a high-frequency filter coupled to the inverter and configured to output the second waveform.

According to a further aspect of any of the above-described embodiments, the inverter includes four switching elements arranged in an H-bridge topology and each of the switching elements may be a wide bandgap field effect transistor.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

A generator according to the present disclosure can operate ultrasonic and electrosurgical instruments at multiple frequencies. In particular, the generator may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator includes electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
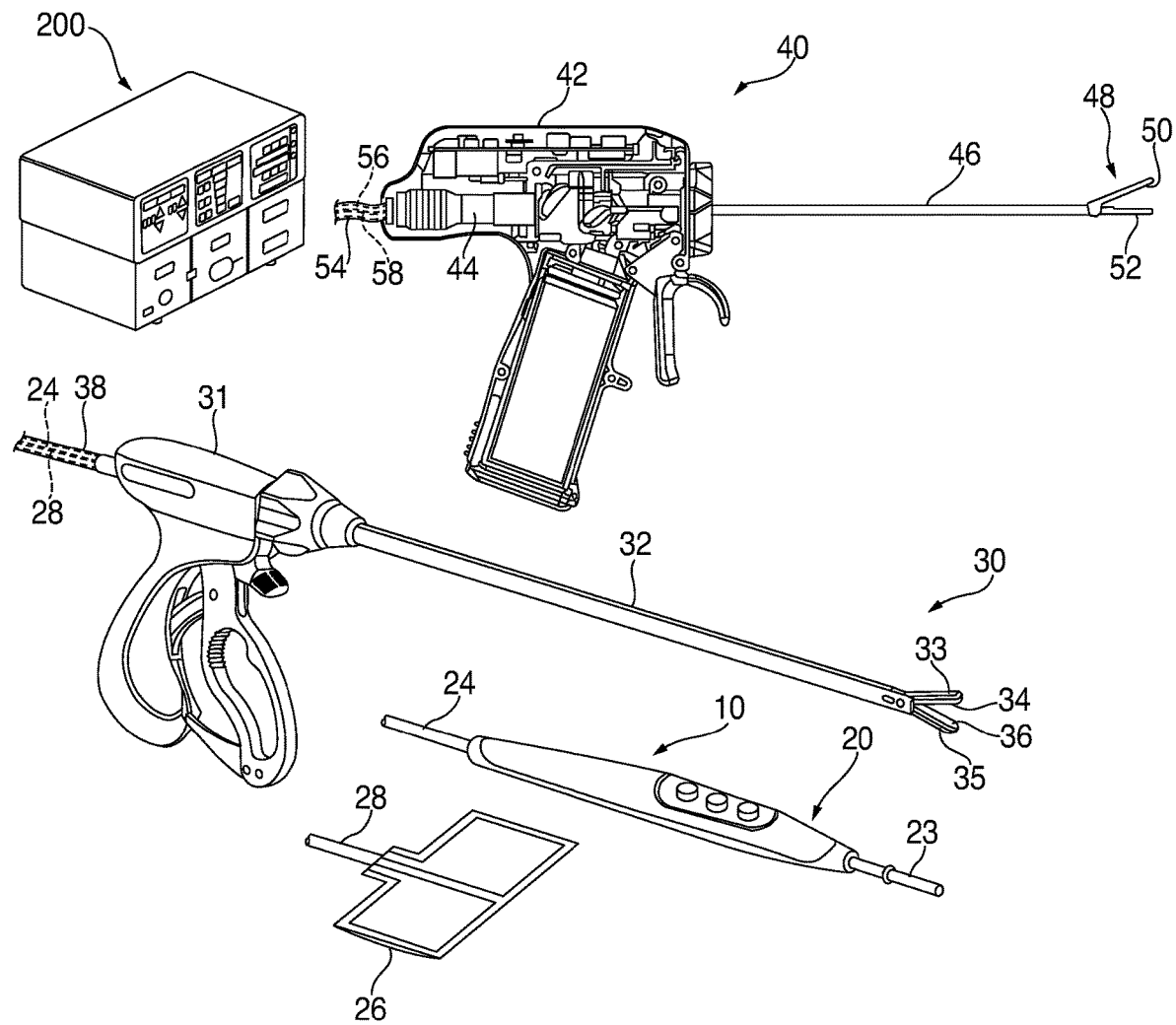
FIG. 1 is a perspective view of a surgical system according to an embodiment of the present disclosure.

FIG. 1 is a perspective view of the components of one illustrative embodiment of a dual-output system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 230 (FIG. 3) of the generator 200, allowing the instrument 20 to cut, coagulate, thermally or non-thermally ablate and/or otherwise treat tissue. The alternating current is returned to the generator 200 through a return electrode pad 26 via a return line 28 at a return terminal 232 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
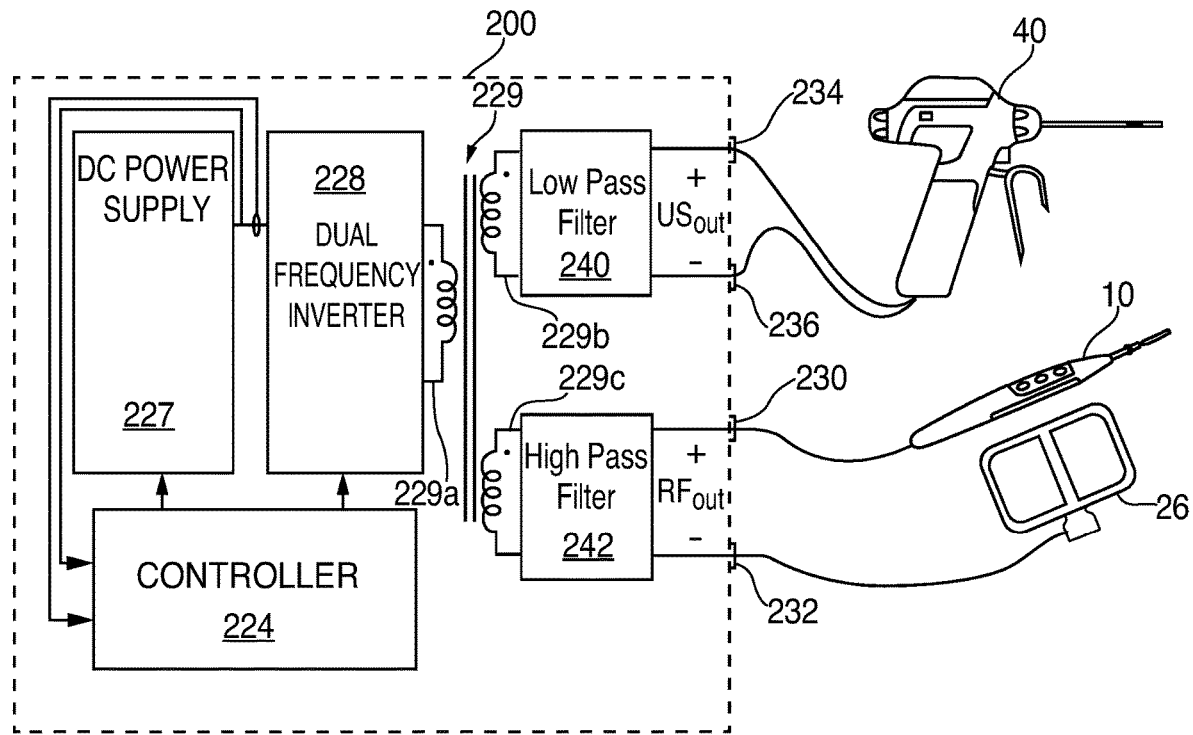
FIG. 3 is a schematic diagram of the dual-output generator of FIG. 2 according to an embodiment of the present disclosure.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 230, 232, respectively (FIG. 3). The electrosurgical forceps 30 is coupled to the generator 200 at a port having connections to the active and return terminals 230 and 232 (e.g., pins) via a plug disposed at the end of the cable 38, wherein the plug includes contacts from the supply and return lines 24, 28 as described in more detail below.

The system 10 also includes an ultrasonic surgical instrument 40, which includes a housing 42 having an ultrasonic transducer 44 disposed therein. The ultrasonic surgical instrument 40 also includes an elongated shaft 46 having an end effector 48 disposed at a distal end thereof. The distal end effector 48 includes a movable jaw member 50 and a probe 52. The ultrasonic transducer 44 is connected to the generator 200 via a cable 54 that includes supply lines 56 and 58 coupled to active and return terminals 234 and 236 (FIG. 3), respectively. The ultrasonic probe 52 is coupled to the ultrasonic transducer 44, such that when the ultrasonic transducer 44 is actuated in response to RF current from the generator 200, the ultrasonic transducer 44 generates ultrasonic mechanical motion within the probe 52, which may be used to seal and/or cut tissue.

Figure 2:
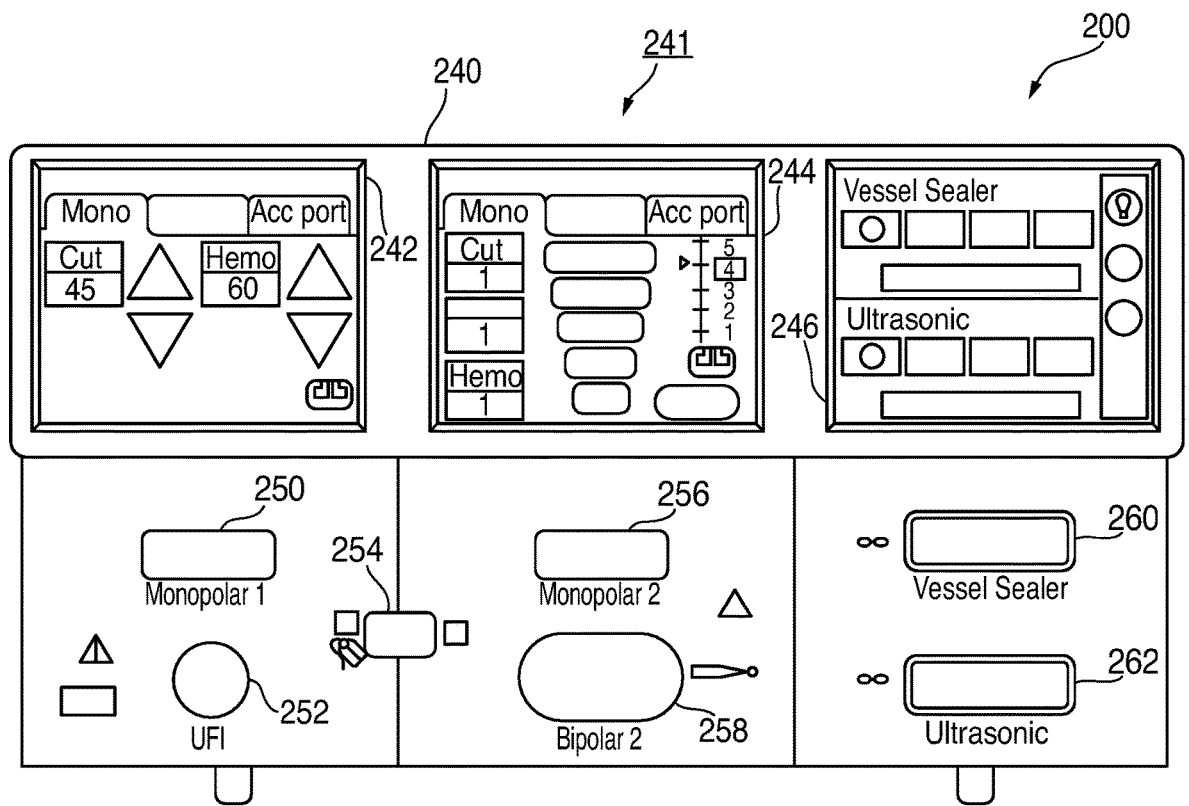
FIG. 2 is a front view of a dual-output generator of FIG. 1 according to an embodiment of the present disclosure.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, ultrasonic surgical instrument 40, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user then adjusts inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional inputs (e.g., replicating inputs of the generator 200). Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 and the ultrasonic surgical instrument 40 that may be plugged into the ports 260 and 262, respectively. The generator 200 outputs energy through the port 260 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to the controller 224 where the setting may be saved in memory 226. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30.

The active and return terminals 230 and 232 and the active and return terminals 234 and 236 may be coupled to any of the desired ports 250-262. In embodiments, the active and return terminals 230 and 232 may be coupled to the ports 250-260 and the active and return terminals 234 and 236 may be coupled to the port 262.

FIG. 3 shows a schematic block diagram of the generator 200 configured to output low-frequency waveform for energizing a first instrument and high-frequency waveform for energizing a second instrument. In particular, FIG. 3 shows the generator 200 is outputting low-frequency waveform to the transducer 44 (FIG. 1) of the ultrasonic surgical instrument 40 and a high-frequency waveform to the monopolar electrosurgical instrument 20 and/or electrosurgical forceps 30. The generator 200 is also configured to output low-frequency energy for energizing any suitable electrosurgical instrument and output high-frequency energy for energizing another electrosurgical instrument. In embodiments, the electrosurgical instruments may be the same (e.g., monopolar electrosurgical instrument 20) such that each of the two electrosurgical instruments is operated at a separate frequency. In further embodiments, the electrosurgical instruments may be different, such that one of the instruments (e.g., monopolar electrosurgical instrument 20) is operated at a low-frequency and another instrument (e.g., electrosurgical forceps 30) is operated at a high-frequency.

The generator 200 includes a controller 224, a power supply 227, and a dual frequency inverter 228. The power supply 227 may be a high voltage, DC power supply connected to an AC source (e.g., line voltage) and provides high voltage, DC power to the dual-frequency inverter 228, which then converts high voltage, DC power into treatment energy (e.g., electrosurgical or ultrasonic) and delivers the energy to the active terminals 230 and 234. The energy is returned thereto via the return terminals 232 and 236. In particular, electrical energy for the ultrasonic instrument 40 is delivered through the active and return terminals 234 and 236 and electrosurgical energy for energizing the monopolar electrosurgical instrument 20 and/or electrosurgical forceps 30 is delivered through the active and return terminals 230 and 232. The active terminals 230, 234 and return terminals 232, 236 are coupled to the dual-frequency inverter 228 through an isolation transformer 229.

The isolation transformer 229 includes a primary winding 229a coupled to the dual-frequency inverter 228, a first secondary winding 229b coupled to a low pass filter 304, and a second secondary winding 229c coupled to a high pass filter 306. The low pass filter 304 is configured to pass through only the low-frequency current generated by the dual-frequency inverter 228, which is then supplied to the active and return terminals 234 and 236. The high pass filter 306 is configured to pass through only the high frequency current generated by the dual-frequency inverter 228, which is then supplied to the active and return terminals 230 and 232. In embodiments, the low pass filter 304 and the high pass filter 306 may be inductor/capacitor filters, which are tuned at their respective resonant frequencies.

The dual-frequency inverter 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Dual-frequency inverter 228 may be a resonant RF amplifier or a non-resonant RF amplifier. A non-resonant RF amplifier, as used herein, denotes an amplifier lacking any tuning components, i.e., conductors, capacitors, etc., disposed between the RF inverter and the filters 304 and 306.

The controller 224 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 224 includes an output port that is operably connected to the power supply 227 and/or dual-frequency inverter 228 allowing the processor to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then controls the power supply 227 and/or dual-frequency inverter 228, which adjusts the DC and/or power supply, respectively, including, but not limited to, field programmable gate array, digital signal processor, and combinations thereof.

The generator 200 according to the present disclosure may also include a plurality of sensors (not shown). The sensors may be coupled to power supply 227 and/or dual-frequency inverter 228 and may be configured to sense properties of DC current supplied to the dual-frequency inverter 228 and/or RF energy outputted by the dual-frequency inverter 228, respectively. Various components of the generator 200, namely, the dual-frequency inverter 228, the current and voltage sensors, may be disposed on a printed circuit board (PCB). The controller 224 also receives input signals from the input controls of the generator 200, the instrument 20 and/or electrosurgical forceps 30. The controller 224 utilizes the input signals to adjust power outputted by the generator 200 and/or performs other control functions thereon.

Figure 4:
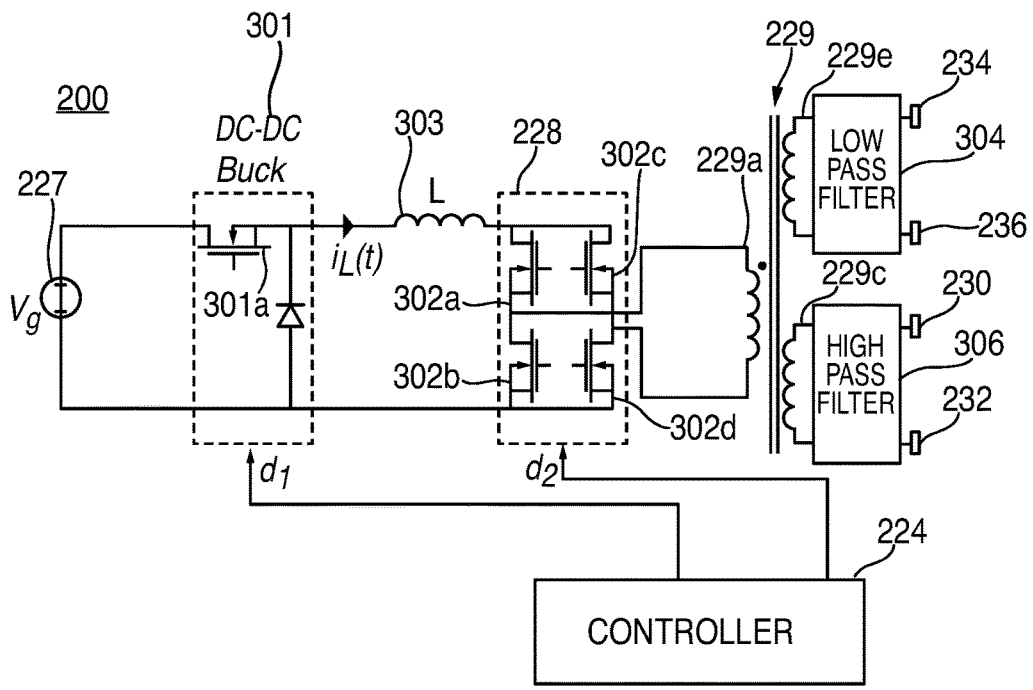
FIG. 4 is an electrical schematic diagram of the dual-output generator of FIG. 2 according to an embodiment of the present disclosure.

With reference to the schematic shown in FIG. 4, the generator 200 includes a DC-DC buck converter 301 and the dual-frequency inverter 228. In the exemplary embodiment, the power supply 227 may be connected to DC-DC buck converter 301. Furthermore, an inductor 303 is electrically coupled between DC-DC buck converter 301 and dual-frequency inverter 228. The output of dual-frequency inverter 228 transmits power to the primary winding 229a of transformer 229, which passes through the secondary winding of transformer 229 to the load, e.g., tissue being treated, the ultrasonic transducer 44, etc.

DC-DC buck converter 301 includes a switching element 301a and dual-frequency inverter 228 includes a plurality of switching elements 302a-302d arranged in an H-bridge topology. In embodiments, dual-frequency inverter 228 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicone carbide, or any other suitable wide bandgap material.

Figure 5:
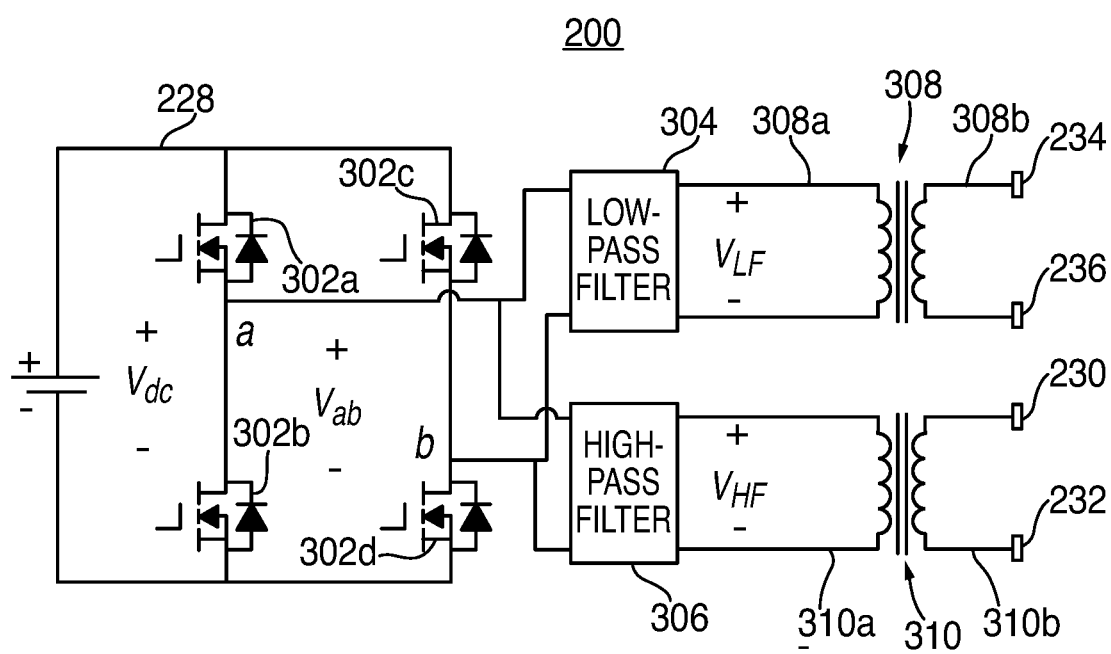
FIG. 5 is a schematic diagram of another embodiment of a DC-AC inverter of the dual-output generator of FIG. 1.

FIG. 5 shows another embodiment of the generator 200, which differs from the embodiment of FIGS. 3 and 4 in that the low pass filter 304 and high pass filter 306 are coupled directly to the dual-frequency inverter 228 rather than the first secondary winding 229b and the second secondary winding 229c of the isolation transformer 229, respectively. Each of the low pass filter 304 and the high pass filter 306 includes an isolation transformer 308 and 310, respectively. The low pass filter 304 is coupled to a primary winding 308a of the isolation transformer 308 and high pass filter 306 is coupled to a primary winding 310a of the isolation transformer 310. The active terminal 234 and return terminal 236 are coupled to a secondary winding 308b of the isolation transformer 308 and the active terminal 230 and the return terminal 232 are coupled to a secondary winding 310b of the isolation transformer 310.

The controller 224 is in communication with both DC-DC buck converter 301 and dual-frequency inverter 228, in particular, the switching elements 301a and 302a-302d, respectively. Controller 224 is configured to output control signals, which may be a pulse-width modulated signal, to switching elements 301a and 302a-302d as described in further detail in co-pending application published as US 2014/0254221, entitled CONSTANT POWER INVERTER WITH CREST FACTOR CONTROL, filed on Dec. 4, 2013 by Johnson et al., the entire contents of which are incorporated by reference herein. In particular, controller 224 is configured to modulate a control signal $d_1$ supplied to switching element 301a of DC-DC buck converter 301 and control signals $d_2$ supplied to switching elements 302a-302d of dual-frequency inverter 228. Additionally, controller 224 is configured to measure power characteristics of generator 200, and control generator 200 based at least in part on the measured power characteristics. Examples of the measured power characteristics include the current through inductor 103 and the voltage at the output of dual-frequency inverter 228. In an exemplary embodiment, controller 224 controls buck converter 301 by generating the control signal $d_1$ based on a comparison of the inductor current and a nonlinear carrier control current for every RF cycle.

The generator 200 according to the present disclosure, and in particular, the controller 224 is configured to operate the dual-frequency inverter 228 using a dual-frequency selective harmonic elimination ("DFSHE") modulation method. Moreover, the DFSHE modulation according to the present disclosure is applicable to a variety of DC/AC topologies, such as half-bridge, full bridge, multilevel inverter, and resonant type inverters and the dual-frequency inverter 228 is an exemplary embodiment. In DFSHE modulation, the controller 200 signals the dual-frequency inverter 228 to generate two individual frequencies, while diminishing undesired harmonics. The controller 224 is configured to generate a pulse-width modulated control signals to the switching elements 302a-302d. Each of the control signals is based on switching angles for each of the switching elements 302a-302d, which when activated generate a low-frequency waveform for energizing the transducer 44 or any other suitable instrument, such as the monopolar electrosurgical instrument 20 or the electrosurgical forceps 30. The low-frequency waveform may have a fundamental frequency from about 10 kHz to about 100 kHz, in embodiments, from about 30 kHz to about 70 kHz. The low-frequency waveform also generates a plurality of harmonic waveform. Since not all of the resulting waveforms are suitable, only one of the higher harmonic waveforms may be used in addition to the fundamental waveform. In particular, a kth harmonic waveform, which is a high frequency waveform, may be used for energizing one of the electrosurgical instruments, such as, the monopolar electrosurgical instrument 20 or the electrosurgical forceps 30. Thus, the switching angles for activating the switching elements 302a-302d are selected that generate the low-frequency waveform and a high frequency waveform, which is a kth harmonic of the low-frequency waveform.

Figure 6:
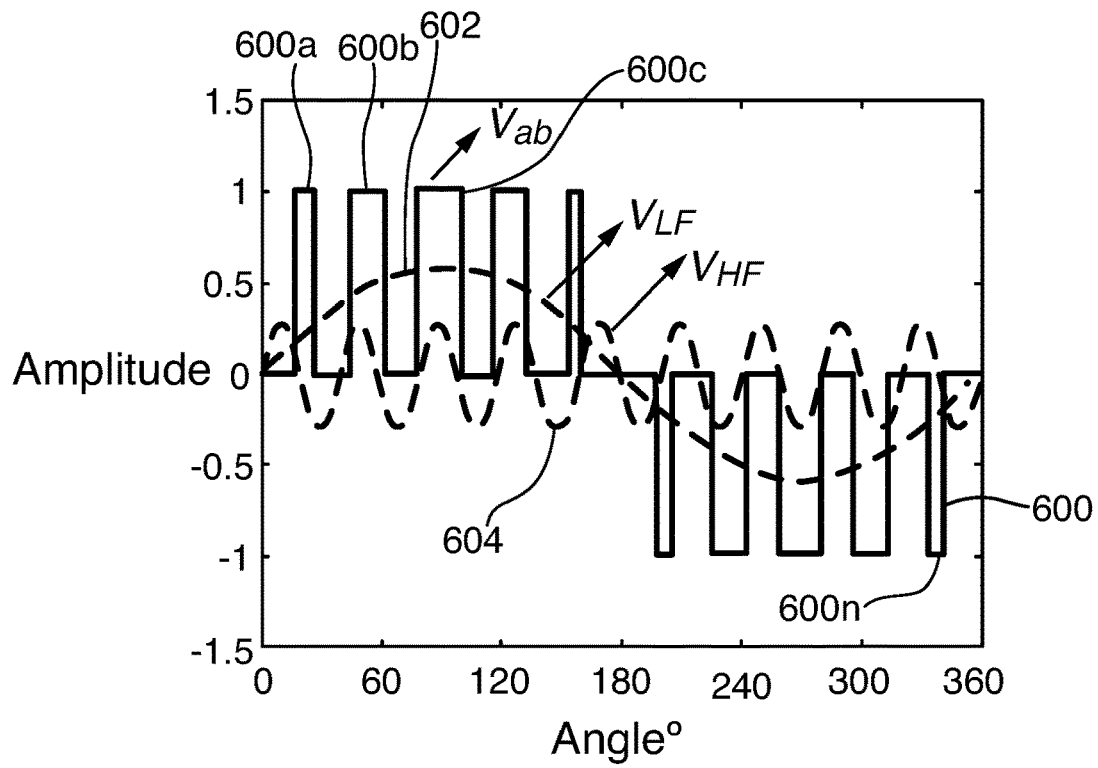
FIG. 6 is a plot of a unipolar switching angle waveform for generating a sinusoidal low frequency waveform and a high frequency waveform according to an embodiment of the present disclosure.
Figure 7:
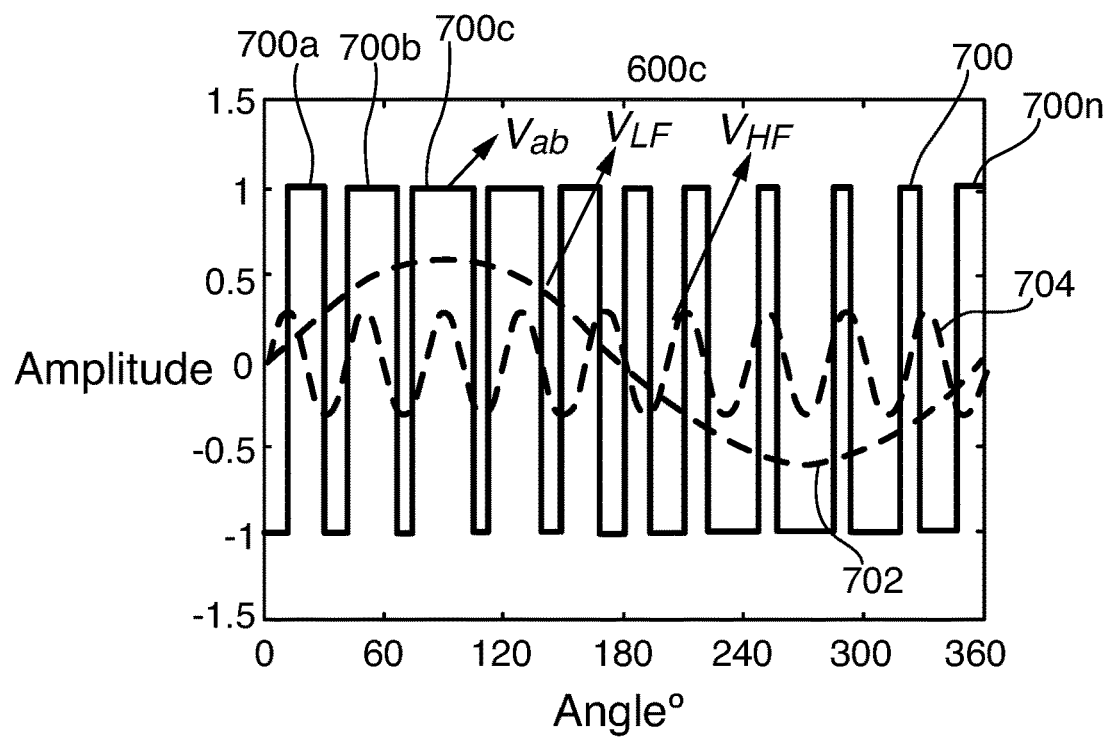
FIG. 7 is a plot of a bipolar switching angle waveform for generating a sinusoidal low frequency waveform and a high frequency waveform according to an embodiment of the present disclosure.

With reference to FIGS. 6 and 7, exemplary switching angle waveforms for generating dual-frequency outputs are shown. FIG. 6 shows a quarter symmetric, unipolar switching angle waveform 600 for generating a sinusoidal low frequency waveform 602 and a sinusoidal high frequency waveform 604. The unipolar switching angle waveform 600 includes a plurality of pulses 600a, b, c, . . . n corresponding to the switching angles for each of the switching elements 302a-302d (FIGS. 4 and 5). The pulses of the switching angle waveform 600 also correspond to the positive and negative cycles of each of the low frequency waveform 602 and a high frequency waveform 604.

All of the positive and negative cycles of the unipolar switching angle waveform 600 produce the positive and negative cycles of the low frequency waveform 602. In particular, there are multiple switching pulses 600a, b, c, . . . n of varying duration per period of the low frequency waveform 602 and the high frequency waveform 604. The term "period" as used herein denotes the time it takes to complete one full cycle of a waveform. Thus, for each period of the low frequency waveform 602, there are ten (10) switching pulses 600a, b, c, . . . n, five (5) per half cycle/period and the switching pulses 600a, b, c, . . . n are of different duration. Similarly, for each period of the high frequency waveform 604 there is at least one complete and one partial switching pulse of different duration as illustrated in FIG. 6. Each of the pulses 600a, b, c, . . . n be calculated by the controller 224 based on a desired frequencies of the low frequency waveform 602 and the high frequency waveform 604.

FIG. 7 shows a quarter symmetric bipolar switching angle waveform 700 for generating a sinusoidal low frequency waveform 702 and a sinusoidal high frequency waveform 704. The bipolar switching angle waveform 700 includes a plurality of pulses 700a, b, c, . . . n corresponding to the switching angles for each of the switching elements 302a-302d. The pulses of the switching angle waveform 700 also correspond to the positive and negative cycles of each of the low frequency waveform 702 and a high frequency waveform 704.

All of the positive and negative cycles of the bipolar switching angle waveform 700 produce the positive and negative cycles of the low frequency waveform 702. In particular, there are multiple switching pulses 700a, b, c, . . . n of varying duration per period of the low frequency waveform 702 and the high frequency waveform 704. Thus, for each period of the low frequency waveform 702, there are ten (10) switching pulses 700a, b, c, . . . n, five (5) per half cycle/period and the switching pulses 700a, b, c, . . . n are of different duration. Similarly, for each period of the high frequency waveform 704 there is at least one complete and one partial switching pulse of different duration as illustrated in FIG. 7. The pulses 700a, b, c, . . . n are of varying duration and may be calculated by the controller 224 based on a desired frequencies of the low frequency waveform 702 and the high frequency waveform 704.

Frequencies of each of the low frequency waveforms 602, 702 and the high frequency waveforms 604, 704 may be set by a user using the user interface 241. The controller 224 may then calculate the switching angles for generating the waveforms 602, 604, 702, and 704. In particular, the controller 224 may calculate the number, frequency, and duration of the switching angles, e.g., duration of the pulses 600a, b, c, . . . n and 700a, b, c, . . . n. In embodiments, these properties may be calculated offline either by the controller 224 or any other suitable processor.

Figure 8:
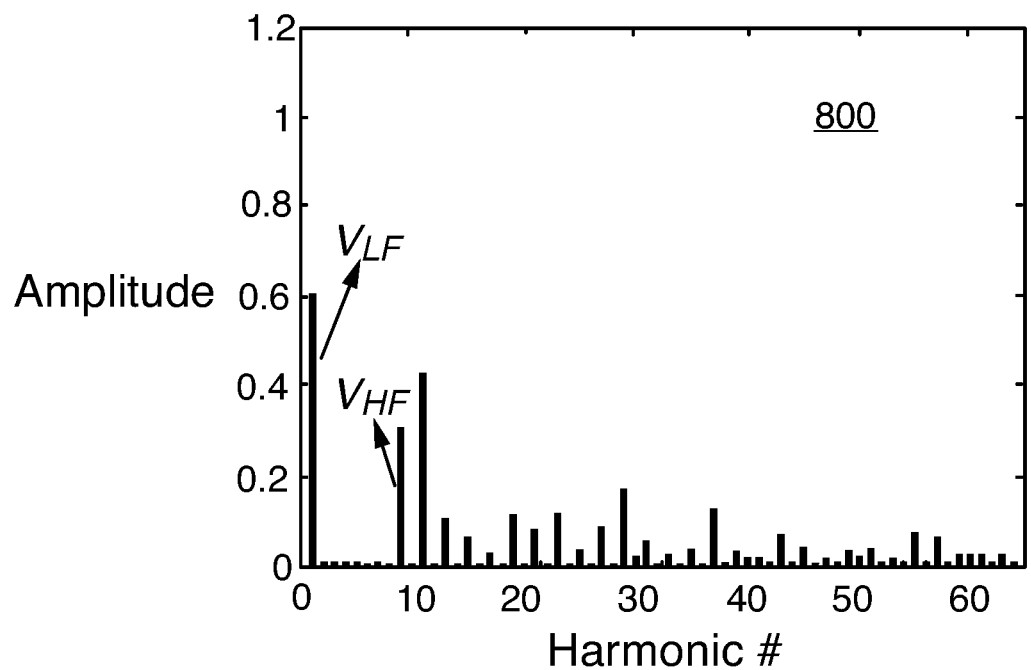
FIG. 8 is a bar graph of harmonic frequencies of the waveforms generated by the unipolar switching angle waveform of FIG. 6.
Figure 9:
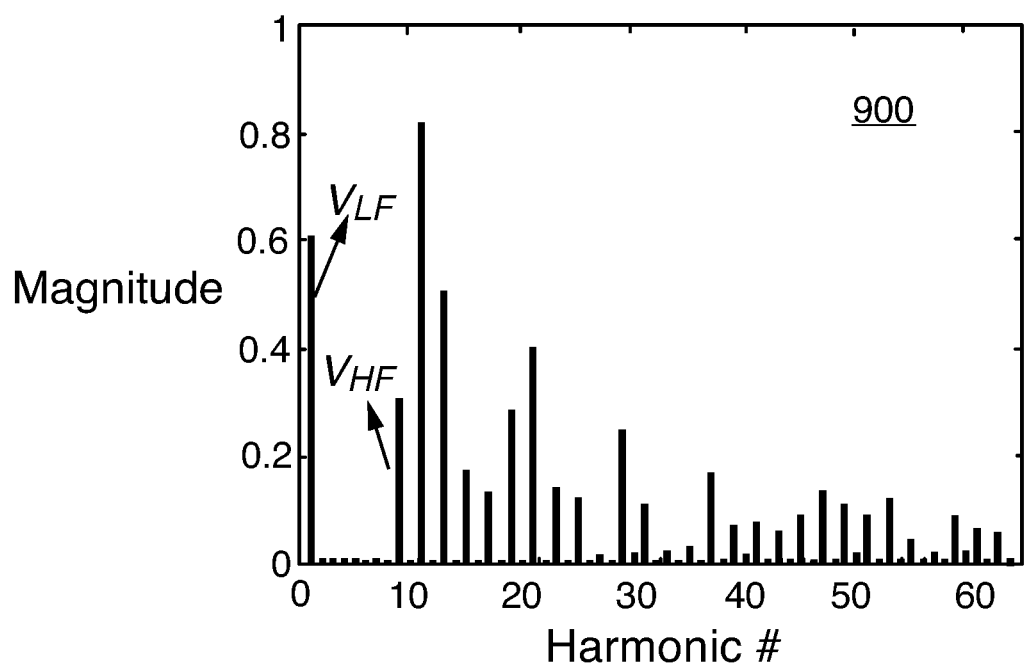
FIG. 9 is a bar graph of harmonic frequencies of the waveforms generated by the bipolar switching angle waveform of FIG. 7.

FIGS. 8 and 9 show harmonic frequency plots 800 and 900 generated by the switching angle waveforms 600 and 700, respectively. The plots 800 and 900 are bar graphs illustrating the frequency content of the waveforms 600 and 700, respectively, number of harmonics and their amplitude. The fundamental frequency waveform is shown as the first bar in each of the plots 800 and 900 and is the low frequency waveform 602 and 702. The high frequency waveforms 604 and 705 are higher kth harmonic waveforms. The plots 800 and 900 also show that the DFSHE modulation method also eliminates all of the harmonic waveforms between the low frequency waveforms 602, 702 and high frequency waveforms 604, 704.

To decouple and control the amplitude of simultaneous waveforms 602, 604 and 702, 704, the present disclosure utilizes a DFSHE modulation method, which allows for fundamental and certain harmonics to be independently controlled. This also allows for individual power regulation and elimination of undesired harmonics, which reduces energy losses and electro-magnetic interference. The pulses 600a, b, c, . . . n of the quarter symmetric unipolar waveform 600 are calculated using DFSHE algorithm according to the present disclosure. Fourier expansion of this switching angle waveforms 600 or 700 may be done using the formula (1) below:

$$v(\omega t) = \sum_{n=1,3,5,...}^{\infty} \frac{4V_{dc}}{n\pi} [\cos(n\theta_1) - \cos(n\theta_2) + \cos(n\theta_3) - ... + \cos(n\theta_m)] \cdot \sin(n\omega t) \quad (1)$$

Since the two components, namely, the waveforms 602 and 604 or the waveforms 702 or 704, to be synthesized are a low-frequency element and its kth harmonic. Under these conditions, the Fourier expansion of (1) is rearranged to form a system of equations as illustrated in formula (2) below:

$$\begin{cases} \frac{4V_{dc}}{\pi}(\cos\theta_1 - \cos\theta_2 ... + \cos\theta_m) = V_{LF} \\ \cos3\theta_1 - \cos3\theta_2 ... + \cos3\theta_m = 0 \\ \cos5\theta_1 - \cos5\theta_2 ... + \cos5\theta_m = 0 \\ \frac{4V_{dc}}{k\pi}(\cos k\theta_1 - \cos k\theta_2 ... + \cos k\theta_m) = V_{HF} \\ ... \\ \cos n\theta_1 - \cos n\theta_2 ... + \cos n\theta_m = 0 \end{cases} \quad (2)$$

Solving formula (2) generates the switching angles, namely, pulses 600a, b, c, . . . n or pulses 700a, b, c, . . . n, for synthesizing the desired dual-frequency output. In embodiments, two solver loops may be employed to solve the transcendental equations of formula (2).

In traditional PWM modulation schemes, only fundamental frequency waveform is generated and controlled, while unregulated harmonics are filtered. In the DFSHE modulation according to the present disclosure, however, both fundamental frequency waveform, e.g., low frequency waveform 602 or 702, and the kth harmonic waveforms, e.g., high frequency waveforms 604 and 704, are simultaneously generated and accurately modulated, and undesired harmonics, namely, frequencies between, below, and/or near the desired frequencies are eliminated. As illustrated in FIGS. 8 and 9, the DFSHE modulation according to the present disclosure, allows for regulation of the waveform amplitude at all frequencies between the low and high controlled frequencies to zero. In addition, harmonics above the selected highest controlled frequency may also be eliminated.

Moreover, unlike harmonic utilization techniques, the fundamental and the kth harmonic waveforms are decoupled in modulation, which provides for individual power regulation of these waveforms. These features of DFSHE modulation according to the present disclosure make it particularly useful in electrosurgical generators, which previously relied on dual-inverter configurations to achieve dual-frequency output. Compared with multilevel inverters or dual-inverter configurations, another advantages of the generators, systems, and method according to the present disclosure is that no additional switching devices are required, which significantly reduces overall costs while achieving equivalent regulation performance.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A dual-output electrosurgical generator, comprising:
a power supply configured to output a direct current (DC) waveform;
an inverter coupled to the power supply, the inverter including at least one switching element operated at a switching angle; and
a controller coupled to the inverter and configured to modulate the switching angle using dual-frequency selective harmonic elimination modulation to simultaneously generate a first waveform at a first frequency and a secondary waveform at a second frequency and eliminate at least one harmonic waveform between the first frequency and the second frequency.

2. The dual-output electrosurgical generator according to claim 1, wherein the first frequency is a fundamental frequency.

3. The dual-output electrosurgical generator according to claim 2, wherein the second frequency is a harmonic frequency of the fundamental frequency.

4. The dual-output electrosurgical generator according to claim 1, further comprising:
a low-frequency filter coupled to the inverter and configured to output the first waveform.

5. The dual-output electrosurgical generator according to claim 1, further comprising:
a high-frequency filter coupled to the inverter and configured to output the second waveform.

6. The dual-output electrosurgical generator according to claim 1, wherein the at least one switching element includes four switching elements arranged in an H-bridge topology.

7. The dual-output electrosurgical generator according to claim 6, wherein each of the switching elements is a wide bandgap field effect transistor.

8. The dual-output electrosurgical generator according to claim 1, wherein the second frequency is higher than the first frequency.

9. An electrosurgical system, comprising:
a dual-output electrosurgical generator including:
a power supply configured to output a direct current (DC) waveform;
an inverter coupled to the power supply, the inverter including at least one switching element operated at a switching angle;
a controller coupled to the inverter and configured to modulate the switching angle using dual-frequency selective harmonic elimination modulation to simultaneously to generate a first waveform at a first frequency and a secondary waveform at a second frequency and eliminate at least one harmonic waveform between the first frequency and the second frequency;
a first output outputting the first waveform; and
a second output outputting the second waveform;
a first instrument coupled to the first output and energizable by the first waveform; and
a second instrument coupled to the second output and energizable by the second waveform.

10. The electrosurgical system according to claim 9, wherein the first instrument is an ultrasonic instrument including a transducer energizable by the first waveform.

11. The electrosurgical system according to claim 9, wherein the first instrument is a first electrosurgical instrument including at least one first electrode configured to contact tissue and transmit the first waveform thereto.

12. The electrosurgical system according to claim 9, wherein the second instrument is an electrosurgical instrument including at least one second electrode configured to contact tissue and transmit the second waveform thereto.

13. The electrosurgical system according to claim 9, wherein the first frequency is a fundamental frequency.

14. The electrosurgical system according to claim 13, wherein the second frequency is a harmonic frequency of the fundamental frequency.

15. The electrosurgical system according to claim 9, wherein the dual-output electrosurgical generator further includes a low-frequency filter coupled to the inverter and configured to output the first waveform.

16. The electrosurgical system according to claim 9, wherein the dual-output electrosurgical generator further includes a high-frequency filter coupled to the inverter and configured to output the second waveform.

17. The electrosurgical system according to claim 9, wherein the at least one switching element includes four switching elements arranged in an H-bridge topology.

18. The electrosurgical system according to claim 17, wherein each of the switching elements is a wide bandgap field effect transistor.

19. The electrosurgical system according to claim 9, wherein the second frequency is higher than the first frequency.

* * * * *